United States Patent [19]

Basin et al.

[11] 4,301,365
[45] Nov. 17, 1981

[54] APPARATUS FOR CONTACTLESS MEASUREMENT OF THE THICKNESS OF A SHEET MATERIAL

[76] Inventors: Leonid A. Basin, ulitsa Valikhanova, 6, kv. 2; Alexei A. Valkov, ulitsa Rudneva, 199; Vladimir I. Panin, ulitsa Saina, 6, kv. 162; Vladimir I. Terekhin, ulitsa M. Toreza, 43, kv. 62, all of Alma-Ata, U.S.S.R.

[21] Appl. No.: 78,663

[22] Filed: Sep. 24, 1979

[51] Int. Cl.³ ............................................. G01N 23/00
[52] U.S. Cl. ................................. 250/308; 250/358 R; 250/359
[58] Field of Search .................... 250/308, 358 R, 359, 250/360

[56] References Cited

U.S. PATENT DOCUMENTS 3,662,174  5/1972  McMullen et al. ................. 250/360

Primary Examiner—Davis L. Willis
Attorney, Agent, or Firm—Steinberg & Raskin

[57] ABSTRACT

An apparatus for contactless measurement of the thickness of a sheet material comprises a radioactive source located in a protective container which has a collimating hole to output a flow of radiation. There is a radiation detector to sense the radiation passed through the material under control, which is electrically connected to a radiation intensity meter, and also compressed air means for delivery of a jet of compressed air to the measurement point.

3 Claims, 3 Drawing Figures

APPARATUS FOR CONTACTLESS MEASUREMENT OF THE THICKNESS OF A SHEET MATERIAL

FIELD OF THE INVENTION

The invention relates to measurement engineering, and more particularly to apparatus for contactless measurement of the thickness of sheet materials. The invention is suitable for use in fur industry for sorting furs according to leather thickness.

DESCRIPTION OF THE PRIOR ART

At the enterprises of fur industry the sorting of furs is accomplished by means of organoleptic method and the thickness of the leather is measured in laboratories on a random basis, with the hair covering previously removed.

The described method is disadvantageous in that no objective data on the leather thickness is provided, accuracy is low and the quality of the finished products is therefore less than satisfactory.

Known in the art is an apparatus for contactless measurement of the thickness of a sheet material, comprising a radioactive source located in a cavity of a protective container, said cavity being communicated with the atmosphere via a collimating hole, a radiation detector aligned with the axis of the beam of radiation emanating from the collimating hole, and a radiation intensity meter electrically coupled to the output of the detector and having a scale calibrated in terms of material thickness (cf. Great Britain Pat. No. 1,058,583. Int.Cl.G1A).

The known apparatus can be used for measuring the thickness of materials having an even surface structure, for example, metallic bands, cardboard, paper and the like.

With the known apparatus used directly for measuring the thickness of the leather of furs, great errors occur due to the length and thickness of the hair, density of down or matted hair, etc. Another difficulty consists in that the hair covering and the leather have practically the same chemical element composition, with the result that the variation of the intensities of the radiation passed through a fur skin, as referred to absorption by the leather and the hair covering, cannot be distinguished.

SUMMARY OF THE INVENTION

An object of the invention is to provide an apparatus for contactless measurement of sheet material, capable of measuring the thickness of the leather of a fur skin without removal of the hair covering.

There is provided an apparatus for contactless measurement of sheet material, comprising a radioactive source located in a cavity of a protective container with a collimating hole, a radiation detector positioned after the collimating hole in axial relation to the axis of the beam of radiation emanating from the collimating hole, and a radiation intensity meter connected electrically to an output of the detector, which apparatus is provided, according to the invention, with compressed air means for delivery of compressed air to the sheet material at the measurement point.

Preferably, the compressed air means should communicate with the cavity of the protective container.

Advantageously, the collimating hole is implemented in the form of a slit.

The apparatus of the invention makes it possible to mechanize the measurement of the thickness of the leather of furs before they are subject to dressing, with the result that the production rate and quality of the finished products are increased.

DESCRIPTION OF THE DRAWINGS

The invention will now be described in more detail, by way of example, with reference to the accompanying drawings in which.

DESCRIPTION OF THE INVENTION

Figure 1:
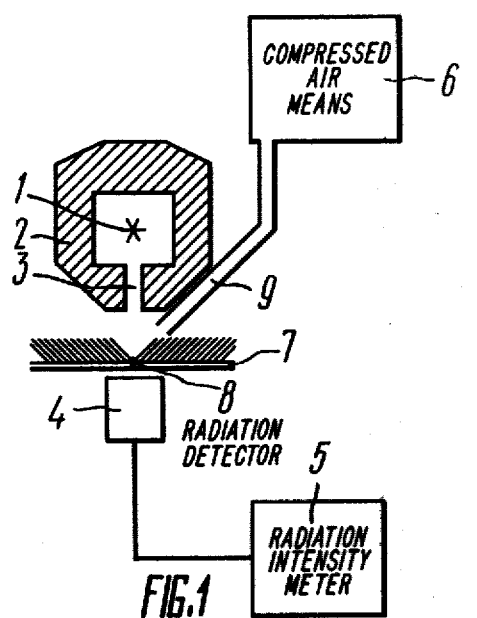
FIG. 1 is a block diagram of an apparatus for contactless measurement of the thickness of a sheet material, according to the invention.

The apparatus of the invention (FIG. 1), adapted to measure the thickness of the leather of furs, comprises a radioactive source 1 located in a cavity of a protective container 2 which has a collimating hole 3. A radiation detector 4 is positioned after the collimating hole 3 in axial relation to the beam of radiation which emanates from the collimating hole and is electrically coupled to an input of a radiation intensity meter 5. The apparatus also comprises compressed air means 6 for delivering a jet of compressed air onto a fur skin 7 at a measurement point 8 with the aid of a nozzle 9.

Figure 2:
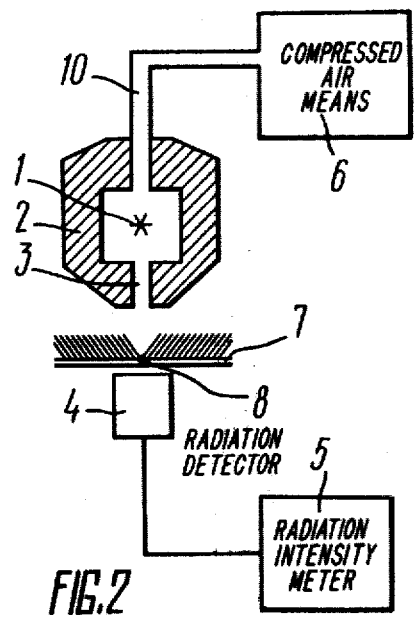
FIG. 2 is a block diagram of another version of the apparatus in which a compressed air means communicates with the cavity of the protective container, according to the invention.

The apparatus of FIG. 2 has the compressed air means 6 communicating with the cavity of the container 2 via a duct 10. The collimating hole 3 serves as a supply nozzle. This version of the apparatus is easy to fabricate and provides for better formation of the compressed air jet.

Figure 3:
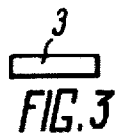
FIG. 3 shows the shape of the collimating hole, according to the invention.

FIG. 3 illustrates a preferred shape of the outlet cross-section of the collimating hole 3. Such an arrangement allows for greater measurement accuracy due to an increase in a ratio of the area of a fur skin with the blown-out hair covering to the whole measurement area. The receiving hole of the detector 4 must have a shape analogous to that of the collimating hole 3 so as to avoid scattered radiation entering into the detector.

The apparatus of the invention operates in the following manner. A fur skin 7 (FIGS. 1,2) is positioned between the source 1 and the detector 4 in a manner that its hair covering faces the source 1. With the compressed air means 6 activated, the compressed air jet is directed at the measurement point 8, with the result that the hair covering is moved aside and the leather of the fur skin is thus exposed. This provides for lesser influence of the hair covering on the absorption of the radiation. The intensity of the radiation is attenuated in passing through the fur skin 7 and is registered by the detector 4 which produces electric signals and the radiation intensity meter 5 then reads the thickness of the leather of the fur skin.

The operation of the proposed apparatus relies on a unique relationship between the thickness of the leather of the fur skin 7 at the measurement point 8 and the intensity I of the radiation passed through that skin and registered by the detector 4.

$$I = I_0 e^{-\mu l}$$

wherein $I_o$ is the intensity of the radiation registered by the detector 4 when no fur skin 7 is present: $\mu$ is a constant which depends on the type and energy of the radiation: and 1 is the length of the fur skin being measured.

What is claimed is:

1. Apparatus for contactless measurement of the thickness of sheet material comprising: a radioactive source; a protective container having a cavity accommodating said radioactive source; a collimating hole in said protective container through which a beam of radiation is directed; a radiation detector, said radiation detector having a receiving hole arranged in axial relation to said beam of radiation in opposed relationship to said collimating hole; a radiation intensity meter having an input electrically coupled to an output of said radiation detector; and compressed air means for directing a jet of compressed air substantially in the direction of said beam to an area where said radiation beam intersects said sheet material during the measurement of the thickness thereof such that said compressed air jet impinges on said sheet material in the area where said radiation beam intersects said sheet material.

2. Apparatus as claimed in claim 1, wherein said compressed air means communicates with said cavity of said protective container and said collimating hole comprises a component of said compressed air means.

3. Apparatus as claimed in claim 2, wherein said collimating hole has the form of a slit.

* * * * *